United States Patent [19]

Cerwin et al.

[11] Patent Number: 4,545,377
[45] Date of Patent: Oct. 8, 1985

[54] NON-METALLIC, BIO-COMPATIBLE HEMOSTATIC CLIPS (TWO PIECE CONFIGURED TO LOCK TIGHTER THE LARGER THE VESSEL BEING CLOSED)

[75] Inventors: Robert J. Cerwin, Pittstown; John S. Pedlick, Butler, both of N.J.

[73] Assignee: Ethicon, Inc., Somerville, N.J.

[21] Appl. No.: 613,693

[22] Filed: May 24, 1984

Related U.S. Application Data

[62] Division of Ser. No. 422,981, Sep. 24, 1982, abandoned.

[51] Int. Cl.⁴ .................... A61B 17/12; A61B 17/00
[52] U.S. Cl. ........................... 128/325; 128/346
[58] Field of Search ............ 128/325, 326, 346, 334 C

[56] References Cited

U.S. PATENT DOCUMENTS

| | | | |
|---|---|---|---|
| 2,245,030 | 6/1941 | Gottesfeld et al. | 128/346 |
| 3,147,754 | 7/1964 | Koessler | 128/346 |
| 3,175,263 | 3/1965 | Bernstein | 128/346 |
| 3,760,811 | 9/1973 | Andrew | 128/346 |
| 3,916,908 | 11/1975 | Leveen | 128/346 |
| 3,993,076 | 11/1976 | Fogarty | 128/325 |

FOREIGN PATENT DOCUMENTS 2932652  2/1981  Fed. Rep. of Germany ...... 128/346

*Primary Examiner*—Gene Mancene
*Assistant Examiner*—C. W. Shedd
*Attorney, Agent, or Firm*—Robert L. Minier

[57] ABSTRACT

A sterile, two-piece hemostatic clip for occluding vessels. The first piece has a vessel clamping surface and a pair of legs extending from that surface. The second piece has a vessel clamping surface and locks with the first piece so that the vessel clamping surfaces face each other. The clamping surfaces are configured such that the locking forces are increased the greater the stress placed on the vessel clamping surfaces.

2 Claims, 5 Drawing Figures

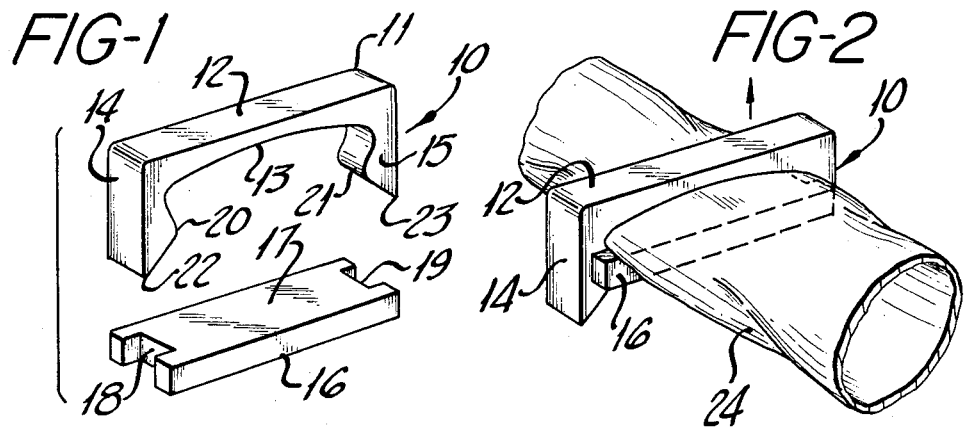
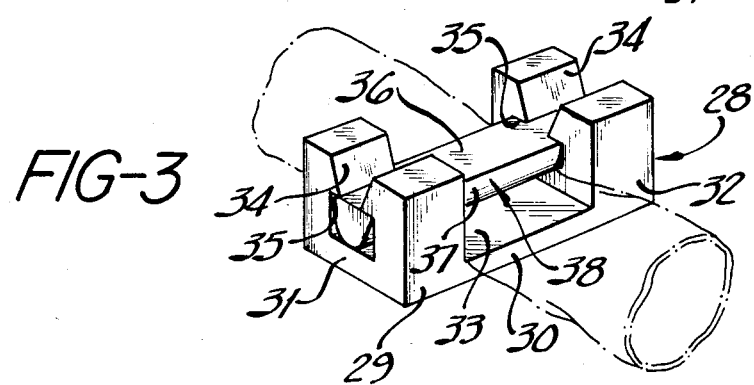
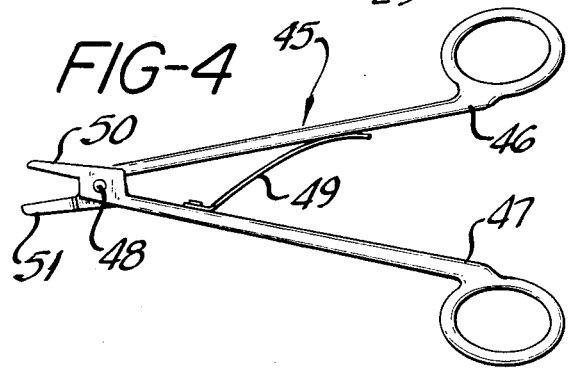
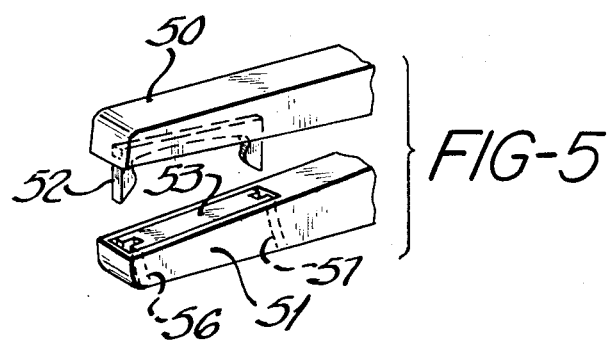

NON-METALLIC, BIO-COMPATIBLE HEMOSTATIC CLIPS (TWO PIECE CONFIGURED TO LOCK TIGHTER THE LARGER THE VESSEL BEING CLOSED)

This is a division of application Ser. No. 422,981, filed Sept. 24, 1982, now abandoned.

The present invention relates to hemostatic clips and more particularly to hemostatic clips fabricated from biocompatible polymeric material which may be absorbable or non-absorbable in body tissue.

BACKGROUND OF THE INVENTION

In many surgical procedures, it is often necessary to ligate a plurality of vessels within the surgical site. The vessels may be severed downstream of the ligated portion. In some instances, a vessel may be ligated in spaced apart areas and the portion of the vessel between the ligations removed. The purpose of ligating vessels is to maintain the surgical site free from an excess of blood and reduce blood loss in the patient. Also in some surgical procedures where tumors and the like are to be removed, the tumor or organ may have to be separated from said vessels. Before separating, the vessels are ligated. Once a blood vessel is completely shut off, hemostatis, that is, the natural closing of the end of the vessel so as to stop blood flow, will occur within several days time depending on the vessel. The body in the meantime will continue to allow blood flow around the ligated area through appropriate capillaries and secondary vessels with the natural pysiological function of the body enlarging these bypass vessels until adequate blood flow is obtained. Hence, when ligating the vessel there should be positive stoppage of the blood flow in the main vessel. Failure to provide complete stoppage may cause blood loss in the patient and may also disrupt the natural hemostatis and concurrent manufacture of new paths of blood flow in the patient.

In the past, the closing of the vessel was usually accomplished using ligatures; that is, filaments or threads which the doctor tied around the vessel to be closed. This is a time-consuming process and one where positive closure of the vessel is not always accomplished. In recent years hemostatic clips have been replaced by ligatures in surgical procedures to close blood vessels and other ovaducts. Very often these hemostatic clips are narrow U or V shaped strips formed of tantalum or stainless steel which are capable of being deformed and possess sufficient strength to retain the deformation while clamped about a blood vessel. Even more recently, hemostatic clips made from biocompatible polymer materials which are either absorbable or non-absorbable in body tissue have been used to ligate vessels. Examples of such polymeric hemostatic clips are disclosed in copending commonly assigned patent application Ser. Nos. 276,131 filed June 22, 1981, and 282,165 filed July 31, 1981.

In most instances, the hemostatic clip should positively close the vessel and stop the flow of blood. The clip should be sufficiently tight about the vessel so that when the surgeon is working in the cavity or area where the vessels have been ligated, the surgeon will not inadvertently remove or disrupt a hemostatic clip either with a sponge or movement of an instrument or the like. The clip should have simple, smooth lines to reduce possible trauma and make the clip relatively easy to manufacture.

What we have discovered is an improved ligating clip structure which, when placed about a vessel, closes the vessel and positively locks the vessel closed. Our new improved hemostatic clip locks tighter to the vessel the larger the vessel and the more pressure placed on the clip by the blood trying to flow through the vessel. Our clip once locked in place is not inadvertently removed or unlocked by being jostled. Our new improved hemostatic clip has simple, smooth lines and is easy to manufacture.

SUMMARY OF THE PRESENT INVENTION

A sterile, two-piece, hemostatic clip for occluding vessels. The clip comprises a first piece having a horizontal or spanning member with a vessel clamping surface. A leg member is disposed from each end of the horizontal member from the same side of the member as the vessel clamping surface and substantially perpendicular thereto. The first piece is adapted to be placed on the vessel to be occluded by placing the leg members on opposite sides of the vessel and the vessel clamping surface in contact with the vessel. The clip includes a second piece having a vessel clamping surface. The second piece is adapted to connect the leg members of the first piece and interlock therewith with the vessel clamping surface in contact with the vessel being occluded. The leg members of the first piece and the second piece combine to render the interlock more secure the greater the stress placed against the vessel clamping surfaces. In certain embodiments of the present invention, the horizontal member of the first piece has a smaller cross-sectional area than the cross-sectional area of the second piece so that the greater the pressure placed on the vessel clamping surfaces of the clip the more the horizontal member is deflected and the more the leg members are urged towards one another and the tighter the two pieces of the clip are held together.

BRIEF DESCRIPTION OF THE DRAWINGS

The present invention will be more fully described in conjunction with the accompanying drawings wherein;

FIG. 1 is an enlarged perspective view of the new two-piece clip of the present invention with the pieces positioned in spaced apart relationship;

FIG. 2 is an enlarged perspective view of the clip of FIG. 1 closed about a blood vessel;

FIG. 3 is an enlarged perspective view of another embodiment of the clip of the present invention closed about the blood vessel;

FIG. 4 is a side view showing an instrument for applying the clips of the present invention; and FIG. 5 is an enlarged perspective view showing the jaws of an instrument used for applying the clips of the present invention.

DETAILED DESCRIPTION OF THE INVENTION

Referring to the drawings, in FIG. 1 there is shown a clip 10 of the present invention. The clip comprises two separate pieces. The first piece 11 has a horizontal or spanning member 12. One surface of the member forms a vessel clamping surface 13. Disposed at opposite ends of the spanning member from the vessel clamping surface are legs 14 and 15. The second piece 16 is a straight member having a vessel clamping surface 17 and has disposed at opposite ends indentations 18 and 19. The indentations are sized to accept the legs. As may be seen, the legs are bulged 20 and 21 outwardly from the surfaces of the legs facing each other adjacent the free end 22 and 23 of each leg. As more clearly shown in FIG. 2, in use, the first piece is placed over the vessel 24 to be occluded or closed and the second piece placed between the legs and forced over the bulges in the legs to occlude the vessel.

As may be seen in FIG. 1, the cross-sectional area of the horizontal member of the first piece is smaller than the cross-sectional area of the second piece. In use, the larger the vessel or the greater the pressure of the blood flowing through the vessel the more the horizontal member of the first piece is deformed outwardly (the direction of the arrow) and the legs of the first piece urged toward each other and the tighter the clip is held in the closed position.

In FIG. 3, there is shown another embodiment of the new two-piece hemostatic clip 28 of the present invention. In this embodiment, the first piece 29 comprises a horizontal member 30 with the U-shaped leg members 31 and 32 extending from opposite ends of the vessel clamping surface 33 of the horizontal or spanning member. Each leg of the U-shaped members has a beveled inner surface 34 extending from the free end of the leg towards the base of the U and terminating at an ear 35. The second piece 36 comprises a straight member having a rounded vessel clamping surface 37 and a flat locking surface 38. The vessel clamping surface of the first piece is placed on the vessel to be occluded. The second piece is pressed between the legs of the U. The legs are deflected outwardly until the flat surface of the piece passes by the ears and is locked in place. When in the locked position, the larger the vessel or the greater the pressure in the vessel, the more faces is applied against the vessel clamping surfaces of the first piece and second piece and the tighter the two pieces are interlocked.

FIG. 4 illustrates a forceps type ligating clip applier 45. The applier comprises two handle members 46 and 47 crossing at a hinge point 48 and maintained in a normally open position by a spring 49. One handle extends beyond the hinge forming jaw member 50 while the extension of the other handle extends beyond the hinge to form a corresponding jaw member 51. As more clearly shown in the enlarged view in FIG. 5, the jaws 50 and 51 are constructed to accept the two pieces 52 and 53 of the clip. The first piece 52 comprises a horizontal member with two leg members and held in the jaw by frictional engagement between the inner side surfaces of the jaw and the side surfaces of the piece. The opposite jaw 51 holds the other piece 53 in place in a similar manner utilizing friction. Openings 56 and 57 are disposed in the jaw 52 adjacent opposite ends of the piece. These openings allow the legs of the first piece to be inserted past the second piece to lock the clip in place about the vessel to occlude the vessel. Once the clip is locked about the vessel, the frictional forces are not sufficient to maintain the piece in the jaws of the clip and the instrument may be readily removed and the clip allowed to remain about the vessel.

The clips of the present invention may be constructed in various sizes according to their intended function. Hemostatic clips are usually less than 6 millimeters in length and 1½ millimeters in length. The dimension of the clip may be reduced by about 50% for certain applications in microsurgery. Larger clips for special hemostatic applications may be about double the size of a typical hemostatic clip. The various sizes of the clip are preferably matched with individual appliers having jaws tailored to the size of the clip for best performance.

The clips of the present invention are most conveniently molded of biologically acceptable polymeric materials which may be absorbable or non-absorbable in body tissue. Preferred absorbable polymers or copolymers include those of glycolide, lactide and poly(p)dioxanone. Preferred non-absorbable polymers include nylon, polyesters, and polypropylene. All these materials have been demonstrated to be biologically acceptable when used as sutures or other implantable medical devices.

The clips are sterilized by any of the well known sterilization techniques and the technique selected will depend to a great extent on the material used to make the clip. Suitable sterilization techniques include heat or steam sterilization, radiation sterilization such as cobalt irradiation, electron beam and the like, ethylene oxide, and other sterilization techniques well known in the art.

The clips of the present invention may be easily and economically manufactured by injection molding or other suitable molding techniques well known in the art.

Having now described the present invention and certain specific embodiments thereof, it will be readily apparent to those skilled in the art that many variations and modifications may be made to the present invention without departing from the spirit and scope thereof.

What is claimed is:

1. A sterile, two-piece hemostatic clip for occluding vessels, said clip comprising a first piece having a spanning member with a vessel clamping surface, a leg member disposed at each end of said spanning member from the same side as said vessel clamping surface, each of said leg members comprising a U-shaped member with the inner facing surfaces of the legs of the U being beveled from their free ends towards the base of the U, said beveled surfaces terminating above the base of the U to form locking ears, said first piece being adapted to be placed on the vessel to be occluded by placing the associated U-shaped legs on opposite sides of the vessel and the vessel clamping inner surface in contact with said vessel and a straight second piece having a vessel clamping surface, said second piece being sized and configured to extend between and fit within each of said U-shaped members and be held in place by said ears.

2. A sterile, two-piece hemostatic clip according to claim 1 wherein the vessel clamping surface of the second piece is rounded.

* * * * *